United States Patent
Zhang et al.

(10) Patent No.: US 11,590,333 B2
(45) Date of Patent: Feb. 28, 2023

(54) TUBULAR COUPLING

(71) Applicant: SAINT-GOBAIN PERFORMANCE PLASTICS CORPORATION, Solon, OH (US)

(72) Inventors: Jianfeng Zhang, Shrewsbury, MA (US); Xipeng Liu, Concord, MA (US); Jian L. Ding, Stow, MA (US)

(73) Assignee: SAINT-GOBAIN PERFORMANCE PLASTICS CORPORATION, Solon, OH (US)

( * ) Notice: Subject to any disclaimer, the term of this patent is extended or adjusted under 35 U.S.C. 154(b) by 0 days.

(21) Appl. No.: 16/254,369

(22) Filed: Jan. 22, 2019

(65) Prior Publication Data
US 2019/0224467 A1     Jul. 25, 2019

Related U.S. Application Data

(60) Provisional application No. 62/620,309, filed on Jan. 22, 2018.

(51) Int. Cl.
*F16L 37/24*      (2006.01)
*A61M 39/10*     (2006.01)
(Continued)

(52) U.S. Cl.
CPC ........... *A61M 39/10* (2013.01); *F16L 37/084* (2013.01); *F16L 37/24* (2013.01); *F16L 37/28* (2013.01);
(Continued)

(58) Field of Classification Search
CPC ......... F16L 37/084; F16L 37/24; F16L 37/28; F16L 37/256; F16L 37/367;
(Continued)

(56) References Cited

U.S. PATENT DOCUMENTS 232,279 A * 9/1880 Lawrence ............. F16L 37/367
                                                 137/614.01
625,783 A * 5/1899 Harris et al. .......... F16L 37/373
                                                 137/637.05
(Continued)

FOREIGN PATENT DOCUMENTS

CN         1898131 A     1/2007
CN       101626803 A     1/2010
(Continued)

OTHER PUBLICATIONS

International Search Report in corresponding PCT/US2009/038103, dated Sep. 28, 2009, 14 pages.
(Continued)

*Primary Examiner* — Craig J Price
(74) *Attorney, Agent, or Firm* — Abel Schillinger, LLP; Chi Suk Kim

(57) ABSTRACT

A tubular coupling comprising a first connector comprising a body defining a first passageway portion and a valve area, the valve area comprising a first volume adjacent to an end of the first passageway portion; and a second volume in fluid communication with the first volume; and a first valve disposed in the first volume of the valve area; and a second connector adapted to receive at least a portion of the first connector, the second connector comprising: a body defining a second passageway portion and a valve area, the valve area comprising: a first volume adjacent to an end of the second passageway portion; and a second volume in fluid communication with the first volume; and a second valve disposed in the first volume of the valve area.

18 Claims, 6 Drawing Sheets

(51) Int. Cl.
  *F16L 37/084* (2006.01)
  *F16L 37/28* (2006.01)
  *A61M 25/00* (2006.01)
  *A61M 39/02* (2006.01)

(52) U.S. Cl.
  CPC ......... *A61M 25/0014* (2013.01); *A61M 39/02* (2013.01); *A61M 2039/1033* (2013.01)

(58) Field of Classification Search
  CPC .......... A61M 2039/1033; A61M 39/10; A61M 39/02; A61M 25/0014; Y10T 137/87925–87973; Y10T 137/9029
  USPC ...... 137/614–614.06, 798; 251/149.1, 149.6, 251/149.9
  See application file for complete search history.

(56) References Cited

U.S. PATENT DOCUMENTS

| | | | |
|---|---|---|---|
| 803,648 A * | 11/1905 | Williams | B27B 25/04 144/242.1 |
| 3,285,627 A * | 11/1966 | Kozulla | F16L 29/005 285/3 |
| 3,486,730 A | 12/1969 | Potash | |
| 3,797,510 A * | 3/1974 | Torres | F16L 55/1007 137/68.14 |
| 3,837,687 A | 9/1974 | Leonard | |
| 3,865,411 A | 2/1975 | Rowe et al. | |
| 3,973,791 A | 8/1976 | Porta et al. | |
| 4,019,512 A | 4/1977 | Tenczar | |
| 4,022,205 A | 5/1977 | Tenczar | |
| 4,030,494 A | 6/1977 | Tenczar | |
| 4,099,748 A | 7/1978 | Kavick | |
| 4,137,930 A | 2/1979 | Scholle | |
| 4,201,208 A | 5/1980 | Cambio, Jr. | |
| 4,256,106 A | 3/1981 | Shoor | |
| 4,265,280 A * | 5/1981 | Ammann | B29C 66/52298 141/98 |
| 4,277,091 A | 7/1981 | Hunter | |
| 4,280,722 A | 7/1981 | Guptil et al. | |
| 4,285,228 A | 8/1981 | Gunning | |
| 4,330,924 A | 5/1982 | Kushner et al. | |
| 4,334,537 A | 6/1982 | Peterson | |
| 4,334,551 A | 6/1982 | Pfister | |
| 4,371,199 A | 2/1983 | Kushner et al. | |
| 4,418,945 A | 12/1983 | Kellogg | |
| 4,423,732 A | 1/1984 | Tarjan et al. | |
| 4,509,554 A * | 4/1985 | Failla | F16L 29/04 137/329.1 |
| 4,610,469 A * | 9/1986 | Wolff-Mooij | A61M 39/26 285/260 |
| 4,620,662 A | 11/1986 | Driggers | |
| 4,717,388 A | 1/1988 | Steer et al. | |
| 4,828,160 A | 5/1989 | Sundholm | |
| 4,946,200 A | 8/1990 | Blenkush et al. | |
| 4,991,882 A | 2/1991 | Gahwiler | |
| 4,993,756 A | 2/1991 | Bechu | |
| 5,067,950 A | 11/1991 | Broadnax, Jr. | |
| 5,087,086 A | 2/1992 | Snedeker | |
| 5,122,123 A | 6/1992 | Vaillancourt | |
| 5,131,696 A | 7/1992 | Sykes et al. | |
| 5,316,041 A | 5/1994 | Ramacier | |
| 5,380,049 A | 1/1995 | Smowton | |
| 5,393,101 A | 2/1995 | Matkovich | |
| 5,404,632 A | 4/1995 | Zaborszki | |
| 5,433,710 A | 7/1995 | VanAntwerp et al. | |
| 5,492,147 A | 2/1996 | Challender et al. | |
| 5,499,439 A | 3/1996 | Zaborszki et al. | |
| 5,511,720 A | 4/1996 | Zaborszki et al. | |
| 5,535,771 A | 7/1996 | Purdy et al. | |
| 5,638,869 A | 6/1997 | Zaborszki et al. | |
| 5,664,759 A * | 9/1997 | Evans | C23C 16/4401 251/63.5 |
| 5,688,254 A | 11/1997 | Lopez et al. | |
| 5,738,144 A * | 4/1998 | Rogers | A61M 39/26 137/614.03 |
| 5,769,558 A | 6/1998 | Jekielek | |
| 5,788,433 A | 8/1998 | Grund et al. | |
| 5,810,398 A | 9/1998 | Matkovich | |
| 5,931,510 A | 8/1999 | Mathew et al. | |
| 6,022,053 A | 2/2000 | Hukuda | |
| 6,106,027 A | 8/2000 | Mulvey et al. | |
| 6,148,849 A | 11/2000 | Green et al. | |
| 6,193,282 B1 | 2/2001 | Assenheimer et al. | |
| 6,341,802 B1 | 1/2002 | Matkovich | |
| 6,394,506 B1 | 5/2002 | Street | |
| 6,488,320 B1 | 12/2002 | Anderson | |
| 6,536,805 B2 | 3/2003 | Matkovich | |
| 6,604,758 B1 | 8/2003 | Assenheimer | |
| 6,655,655 B1 | 12/2003 | Matkovich et al. | |
| 6,814,726 B1 | 11/2004 | Lauer | |
| 6,874,522 B2 | 4/2005 | Anderson et al. | |
| 6,880,801 B2 | 4/2005 | Matkovich et al. | |
| 7,090,191 B2 | 8/2006 | Matkovich et al. | |
| 7,137,974 B2 | 11/2006 | Almasian et al. | |
| 7,358,505 B2 | 4/2008 | Woodworth et al. | |
| 7,396,051 B2 | 7/2008 | Baldwin et al. | |
| 7,677,261 B1 * | 3/2010 | Smith | F16L 37/28 137/1 |
| 7,918,243 B2 | 4/2011 | Diodati et al. | |
| 8,899,267 B2 | 12/2014 | Diodati et al. | |
| 9,062,805 B2 * | 6/2015 | Andrina | F16L 37/367 |
| 9,933,094 B2 * | 4/2018 | Fangrow | A61M 39/18 |
| 10,267,445 B2 * | 4/2019 | Ira | F16L 37/32 |
| 2002/0093192 A1 | 7/2002 | Matkovich | |
| 2003/0127851 A1 | 7/2003 | Guslick et al. | |
| 2004/0034328 A1 | 2/2004 | Unger et al. | |
| 2004/0199143 A1 | 10/2004 | Lauer | |
| 2004/0251683 A1 | 12/2004 | Fisher et al. | |
| 2005/0015075 A1 | 1/2005 | Wright et al. | |
| 2005/0082826 A1 | 4/2005 | Werth | |
| 2005/0090797 A1 | 4/2005 | Almasian et al. | |
| 2006/0142735 A1 | 6/2006 | Whitley | |
| 2006/0217671 A1 | 9/2006 | Peppel | |
| 2007/0025811 A1 | 2/2007 | Wilhelm | |
| 2007/0276356 A1 | 11/2007 | Downing et al. | |
| 2009/0232586 A1 | 9/2009 | Diodati | |
| 2010/0037968 A1 * | 2/2010 | Bisutti | F16K 3/085 137/637.05 |
| 2016/0305574 A1 | 10/2016 | Burdge | |
| 2016/0339224 A1 | 11/2016 | Meise | |

FOREIGN PATENT DOCUMENTS

| | | |
|---|---|---|
| EP | 0719970 B1 | 7/1996 |
| EP | 0739469 B1 | 10/1996 |
| EP | 0795342 A2 | 9/1997 |
| EP | 0966985 A1 | 12/1999 |
| EP | 1096193 A2 | 5/2001 |
| EP | 1162399 A2 | 12/2001 |
| EP | 1184613 A2 | 3/2002 |
| EP | 1326044 A2 | 7/2003 |
| JP | 5079192 A | 6/1975 |
| JP | 622688 U | 3/1994 |
| JP | 2002514941 A | 5/2002 |
| JP | 2004195181 | 7/2004 |
| JP | 2004222888 A | 8/2004 |
| WO | 9010816 A | 9/1990 |
| WO | 9102185 A1 | 2/1991 |
| WO | 9216987 A1 | 10/1992 |
| WO | 9408173 A1 | 4/1994 |
| WO | 9630076 A1 | 10/1996 |
| WO | 9804468 A1 | 2/1998 |
| WO | 0114781 A1 | 3/2001 |
| WO | 2061323 A1 | 8/2002 |
| WO | 2005019566 A2 | 3/2005 |
| WO | 2005019718 A1 | 3/2005 |
| WO | 2009120696 A1 | 10/2009 |

(56) References Cited

FOREIGN PATENT DOCUMENTS

WO        2010142385  A1    12/2010
WO     WO-2018087149  A1  *   5/2018   ............ A61M 39/10

OTHER PUBLICATIONS

International Search Report in corresponding PCT/US2008/001426, dated Jul. 2, 2008, 3 pages.
European Search and Examination Report in corresponding EP 08 725 115.3, dated Aug. 29, 2012, 5 pages.

* cited by examiner

TUBULAR COUPLING

CROSS-REFERENCE TO RELATED APPLICATIONS

This applications claims priority under 35 U.S.C. § 119(e) to U.S. Provisional Patent Application No. 62/620,309, entitled "Tubular Coupling", by Jianfeng Zhang et al., filed Jan. 22, 2018, which is assigned to the current assignee hereof and incorporated herein by reference in its entirety.

FIELD OF THE DISCLOSURE

The present disclosure relates to tubular couplings.

BACKGROUND

Tubular couplings are generally used in joining fluid pathways to form a common fluid conduit. Couplings are typically disposed on terminal ends of tubulars and include connecting members which permit unification of the tubulars. After coupling the tubulars, fluid flow therethrough can be selectively maintained until such point that an operator decides to terminate flow. At such time, the operator can disconnect the coupling to move or reposition the tubulars with respect to one another or a fluid container.

BRIEF DESCRIPTION OF THE DRAWINGS

Embodiments are illustrated by way of example and are not limited in the accompanying figures.

Figure 1:
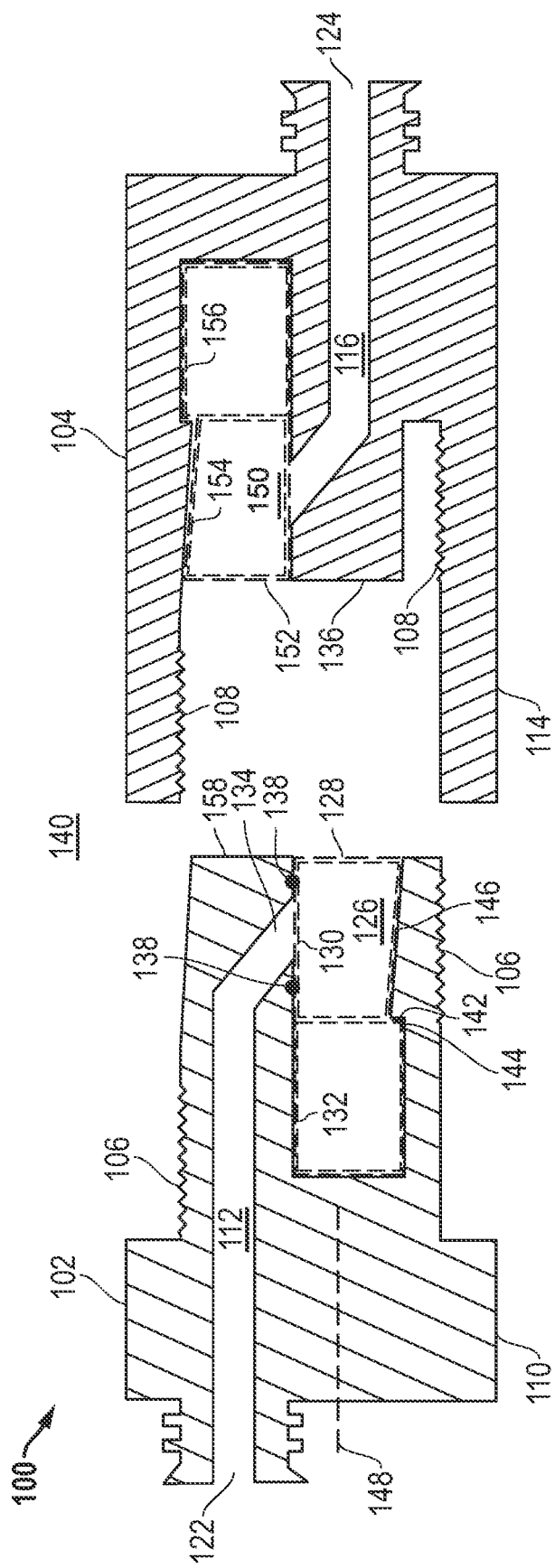
FIG. 1 includes a cross-sectional schematic view of a tubular coupling in accordance with an embodiment prior to coupling a first connector and a second connector.

Skilled artisans appreciate that elements in the figures are illustrated for simplicity and clarity and have not necessarily been drawn to scale. For example, the dimensions of some of the elements in the figures may be exaggerated relative to other elements to help to improve understanding of embodiments of the invention.

DETAILED DESCRIPTION

The following description in combination with the figures is provided to assist in understanding the teachings disclosed herein. The following discussion will focus on specific implementations and embodiments of the teachings. This focus is provided to assist in describing the teachings and should not be interpreted as a limitation on the scope or applicability of the teachings.

As used herein, the terms "comprises," "comprising," "includes," "including," "has," "having," or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

The use of "a" or "an" is employed to describe elements and components described herein. This is done merely for convenience and to give a general sense of the scope of the invention. This description should be read to include one or at least one and the singular also includes the plural, or vice versa, unless it is clear that it is meant otherwise.

Unless otherwise defined, all technical and scientific terms used herein have the same meaning as commonly understood by one of ordinary skill in the art to which this invention belongs. The materials, methods, and examples are illustrative only and not intended to be limiting. To the extent not described herein, many details regarding specific materials and processing acts are conventional and may be found in textbooks and other sources within the coupling arts.

In an embodiment, a tubular coupling includes a first connector and a second connector. The first connector can include a body defining a first passageway portion and a valve area. The valve area can include a first volume adjacent to an end of the first passageway portion and a second volume in fluid communication with the first volume. A first valve can be disposed in the first volume of the valve area. The second connector can be adapted to receive at least a portion of the first connector. By way of a non-limiting example, the first and second connectors can be male-female couplings. The first connector can extend at least partially into the second connector. The second connector can include a body defining a second passageway portion and a valve area. The valve area can include a first volume adjacent to an end of the second passageway portion and a second volume in fluid communication with the first volume. The second connector can also include second valve disposed in the first volume of the valve area. Prior to coupling the first and second connectors together, the first and second valves can be disposed in the first volumes of the valve areas. The first and second valves can translate into the second volumes of the valve areas, for example, when the first and second couplings are urged together. With the first and second valves in the second volumes of the valve areas, the first and second passageways can be in fluid communication with one another.

In an embodiment, first and second connectors can be translated together until the first valve within the first connector moves at least partially, such as fully, from the first volume of the valve area to the second volume of the valve area. Fluid flow can then be initiated.

Figure 2:
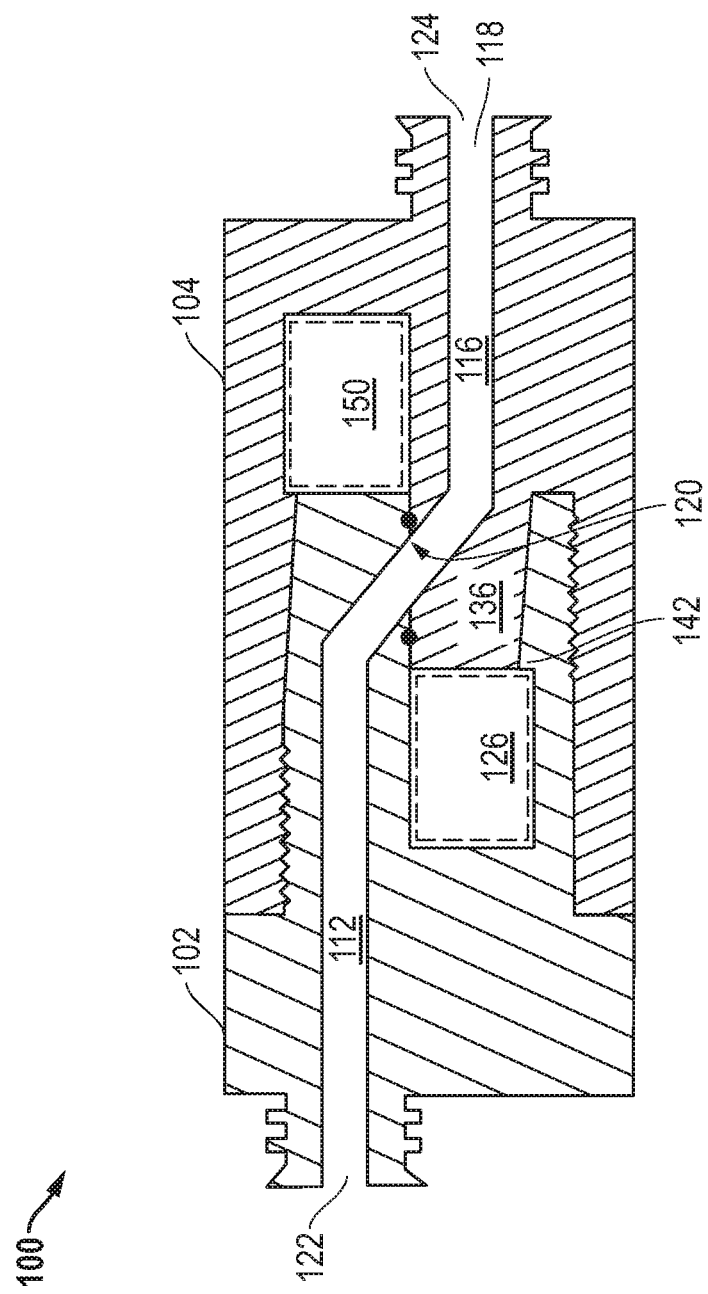
FIG. 2 includes a cross-sectional schematic view of the tubular coupling in accordance with an embodiment after coupling the first connector and the second connector.

Referring now to the figures, FIGS. 1 and 2 include schematic views of a tubular coupling 100 in accordance with an embodiment. The tubular coupling 100 includes a first connector 102 and a second connector 104. In an embodiment, the first connector 102 can be at least partially receivable within the second connector 104 (e.g. male-female connectors). The first and second connectors 102 and 104 can be secured to one another by a threaded or nonthreaded engagement. For example, the first and second connectors 102 and 104 can be secured together by a bayonet connector, interference fit, engageable fasteners, a combination thereof, or another suitable method. The first and second connectors 102 and 104 can be coupled together at a threaded interface 106 and 108. FIGS. 1 and 2 illustrate an embodiment of the tubular coupling 100 including an interference fit.

In an embodiment, the first and second connectors 102 and 104 can remain coupled together after use of the tubular coupling 100. In a more particular embodiment, the first and second connectors 102 and 104 can form a single-use tubular coupling 100. In another embodiment, the first and second connectors 102 and 104 can be detachable from one another, allowing an operator to selectively couple and uncouple the first and second connectors 102 and 104 with respect to one another. In a more particular embodiment, the first and second connectors 102 and 104 can be part of a multi-use, or reusable, tubular coupling 100.

The first connector 102 can include a body 110 defining a first passageway portion 112. The body 110 can include a thermoplastic, a thermoset, a rubber, a metal, another rigid or semi-rigid material, or any combination thereof. By way of example, the body 110 can include polypropylene (PP), PP homopolymer (HPPP), PP copolymer (CPPP), polyethylene (LDPE), Polystyrene (PS), acrylic (PMMA), acrylonitrile butadiene styrene (ABS), polyamide (PA), acetal (POM), polycarbonate (PC), acrylate styrene acrylonitrile (ASA), styrene acrylonitrile (SAN), polyvinyl chloride (PVC), polyurethane (PUR), polyester (PBT or PET), polysulphone (PES), polyphenylene sulphide (PPS), polyvinylidene fluoride (PVDF), polyphenylene oxide (PPO), ethylene vinyl acetate (EVA), or any combination thereof. The body 110 can include epoxy resins, phenolic resins, unsaturated polyester resins, or any combination thereof. In an embodiment, the body 110 can be formed using a machining process. In an embodiment, the body 110 can be formed by injection molding. The body 110 can have a homogenous composition or include two or more nonuniformly distributed materials. In an embodiment, the body 110 is monolithic. In another embodiment, the body 110 includes two or more discrete components coupled together (permanently or removably).

The second connector 104 can include a body 114 defining a second passageway portion 116. The body 114 can include any number of similar features as compared to the body 110 of the first connector 102.

In an embodiment, the first and second passageway portions 112 and 116 together form a passageway 118 between two or more tubulars (not illustrated). In an embodiment, the passageway 118 has a generally S-shaped cross-sectional profile. As illustrated in FIGS. 1 and 2, a junction 120 formed between the first and second passageway portions 112 and 116 can be disposed at a central location of the S-shaped cross-sectional profile. In a non-illustrated embodiment, the junction 120 can be spaced apart from a central location of the S-shaped cross-sectional profile. In a further embodiment, the passageway 118 can be straight. In yet another embodiment, the passageway 118 can include linear segments, curved segments, or a combination thereof.

In an embodiment, the passageway 118 can lie along a line or best-fit line generally parallel with the axis of translation of a first valve (described below). As used with respect to the passageway 118, "generally parallel" refers to an angular deviation of no greater than 10°, or no greater than 8°, or no greater than 6°, or no greater than 4°, or no greater than 2° from parallel. In an embodiment, the passageway 118 can lie along a line or best fit-line that is parallel with the axis of translation of the first valve. In another embodiment, the passageway 118 can lie along a line or best-fit line generally perpendicular with the axis of translation of the first valve. As used with respect to the passageway 118, "generally perpendicular" refers to an angular deviation of no greater than 10°, or no greater than 8°, or no greater than 6°, or no greater than 4°, or no greater than 2° from perpendicular. In yet another embodiment, the passageway 118 can lie along a line that is angularly offset from the axis of translation of the first valve. For example, the passageway 118 can lie along a line having an angular offset from the axis of translation of the first valve in a range of 10° and 80°, in a range of 15° and 75°, in a range of 20° and 70°, in a range of 25° and 65°, in a range of 30° and 60°, in a range of 35° and 55°, or in a range of 40° and 50°.

Fluid ports 122 and 124 on the first and second connectors 102 and 104 can be in fluid communication with the first and second passageway portions 112 and 116, respectively, permitting fluid flow through the passageway 118 between first and second tubulars (not illustrated). The first and second tubulars can engage with the first and second connectors 102 and 104 by any suitable arrangement including, for example, interference fit, clamps, barbed connectors, threaded fasteners, other suitable connection mechanisms, or any combination thereof. In an embodiment, at least one of the fluid ports 122 and 124 is connected to a tubular prior to engagement of the first and second connectors 102 and 104 with one another. In a more particular embodiment, both fluid ports 122 and 124 can be connected to tubulars prior to engagement of the first and second connectors 102 and 104 with one another.

A first valve 126 disposed in a valve area 128 of the first connector 102 can selectively prevent fluid flow through the first passageway portion 112. The valve area 128 can include a first volume 130 and a second volume 132. The first volume 130 can be disposed adjacent to an end 134 of the first passageway portion 112. In a particular embodiment, the first volume 130 and the end 134 of the first passageway portion 112 can be in fluid communication. In a more particular embodiment, the first volume 130 can surround the end 134 of the first passageway 112 such that the first valve 126 at least partially blocks the end 134 of the first passageway portion 112 when the first valve 126 is at least partially disposed in the first volume 130. The second volume 132 can be disposed adjacent to the first volume 130. In an embodiment, the first and second volumes 130 and 132 are in fluid communication with one another.

When disposed in the first volume 130 of the valve area 128, the first valve 126 can prevent fluid flow through the first passageway portion 112. In an embodiment, the first passageway portion 112 can be sterile when the first valve 126 is in the first volume 130. That is, the internal volume of the first passageway portion 112 can be isolated from an external environment and sterilized to create a septic internal environment.

The first valve 126 can translate into the second volume 132 of the valve area 128, for example, upon urging the first and second connectors 102 and 104 together. In the second volume 132, the first valve 126 is spaced apart from the end 134 of the first passageway portion 112. That is, the first passageway portion 112 can be adapted for fluid flow after at least partial displacement of the first valve 126 in a direction from the first volume 130 to the second volume 132. In certain embodiments, fluid flow through the end 134 of the first passageway portion 112 can occur prior to fully displacing the first valve 126 from the first volume 130 to the second volume 132.

In an embodiment, the first valve 126 is adapted to translate from the first volume 126 of the first connector 102 to the second volume 132 of the first connector 102 upon urging the first and second connectors 102 and 104 together. In a more particular embodiment, the second connector 104 can include a portion or feature 136 adapted to bias the first valve 126 from the first volume 130 into the second volume 132. The portion 136 can extend toward the first valve 126 and translate at least partially into the first volume 130 upon coupling the first and second connectors 102 and 104 together. As illustrated, the portion 136 of the second connector 104 can remain disposed at least partially within the first volume 130 of the first connector 102 upon coupling of the first and second connectors 102 and 104.

In an embodiment, the portion 136 is static (i.e., devoid of any moving parts) with respect to the body 114 of the second connector 104. In a particular embodiment, the portion 136 is monolithic with the body 114 of the second connector 104. In another embodiment, the portion 136 can include one or more dynamic parts adapted to move with respect to the body 114 of the second connector 104. As illustrated, the portion 136 can have a shape or size generally corresponding to the shape or size of the first valve 126 where it is to be biased by the portion 136. For example, the portion 136 can have a leading surface (adapted to contact and bias the first valve 126) with an areal size of contact or shape generally equal to the areal size of contact or shape of the first valve 126. In a non-illustrated embodiment, the portion 136 can have a size or shape different from the contact size or shape of the first valve 126. For example, the portion 136 can include a plunger, a tine, a biasing element, a spring, a concave or convex shape, tiered or undulating profile, a specially shaped leading surface, or any combination thereof.

In an embodiment, the first volume 130 of the valve area 128 has a volume, $V_1$, less than a volume, $V_2$, of the second volume 132. For example, in an embodiment, $V_1$ is no greater than 0.99 $V_2$, or no greater 0.95 $V_2$, or no greater than 0.9 $V_2$, or no greater than 0.75 $V_2$, or no greater than 0.5 $V_2$. In another embodiment, $V_1$ is no less than 0.05 $V_2$, or no less than 0.1 $V_2$, or no less than 0.25 $V_2$. $V_1$ can also be in a range between and including any of the values described above with respect to $V_2$. For example, a ratio of $V_1/V_2$ can be in a range of 0.1 and 0.99. In another embodiment, $V_1$ is equal to $V_2$. In yet a further embodiment, $V_1$ is greater than $V_2$.

In an embodiment, the body 110 of the first connector 102 can include an opening (not illustrated) in open communication with the valve area 128. In a more particular embodiment, the opening can be in open communication with the first volume 130 of the valve area 128. In another particular embodiment, the opening can be in open communication with the second volume 132 of the valve area 128. In yet another particular embodiment, the opening can be in open communication with the first and second volumes 130 and 132 of the valve area 128. The opening can permit user observation of the valve area 128 (e.g., to determine position of the first valve 126 within the valve area 128). The second connector 104 can have an opening. The opening of the second connector 104 can be disposed at a similar area of the body 114 as the opening of the first connector 102. In another embodiment, the opening of the second connector 104 can be disposed at a different area of the body 114 as compared to the opening of the first connector 102. For example, the opening in the second connector 104 can be disposed in communication with the second volume 156 of the valve area 152 and the opening in the first connector 102 can be disposed in communication with the first volume 130 of the valve area 128.

A seal 138 can be disposed in the first connector 102, such as adjacent to the end 134 of the first passageway portion 112. The seal 138 can contact the first valve 128 when the first valve 126 is disposed in the first volume 130 of the valve area 128. The seal 138 can be spaced apart from the first valve 126 when the first valve 126 is disposed in the second volume 132 of the valve areas 128.

In an embodiment, the seal 138 is disposed between the first valve 126 and the body 110 of the first connector 102 when the first valve 126 is disposed in the first volume 130 of the valve area 128. In another embodiment, the seal 138 is disposed between the body 110 of the first connector 102 and the body 114 of the second connector 104 when the first valve 126 is disposed in the second volume 132 of the valve area 128.

In an embodiment, the seal 138 can be a ring seal, such as an O-ring. The seal 138 can include a deformable material adapted to occupy a volume of the tubular coupling 100 and prevent fluid flow. In an embodiment, the seal 138 can prevent fluid flow from the first passageway portion 112 when the first valve 126 is disposed in the first volume 130 of the valve areas 128. That is, the seal 138 can seal the first passageway portion 112. In an embodiment, the first passageway portion 112 can maintain a septic state when the seal 138 is properly seated within the first connector.

In an embodiment, the first passageway portion 112 is disconnected from an external environment 140 when the first valve 126 is disposed in the first volume 130 of the valve areas 128. An endcap (not illustrated) can be positioned adjacent to the fluid port 122 to maintain septic state of the first passageway portion 112. In an embodiment, the endcap can be selectively engageable with the first connector 102. For example, the endcap can be connected to the first connector 102 by a threaded or nonthreaded fastener. The endcap can block the fluid port 122, and in concert with the first valve 126 and seal 138 create an airtight first passageway portion 112.

In an embodiment, the first connector 102 can include a retaining feature 142 adapted to maintain the first valve 126 in the second volume 132 of the valve area 128 after the first valve 126 is translated into the second volume 132. In a particular embodiment, the retaining feature 142 can include an end surface 144 of a tapered sidewall 146 defined by the body 110 of the first connector 102. The tapered sidewall 146 can form an angle, as measured with respect to a central axis 148 of the first connector 102, that is at least 1°, or at least 2°, or at least 3°, or at least 4°, or at least 5°, or at least 6°, or at least 7°, or at least 8°, or at least 9°, or at least 10°. In another embodiment, the angle is no greater than 89°, or no greater than 75°, or no greater than 45°, or no greater than 30°, or no greater than 15°. In an embodiment, the tapered sidewall 146 defines a non-rectangular first volume 130 of the valve area 128. That is, a dimension of the first volume 130 at a location adjacent to the second volume 132 can be different from a dimension of the first volume 130 at a location opposite the second volume 132. In a particular embodiment, the first volume 130 has a tapered sidewall. In another embodiment, the cross-sectional dimension of the first volume 130 is less at a location adjacent to the second volume 132 as compared to a location spaced apart from the second volume 132.

In an embodiment, the portion 136 of the second connector 104 can bias the first valve 126 into the second volume by deforming at least one of the first valve 126 and body 102 of the first connector 102 such that the first valve 126 passes over the tapered sidewall 146. As illustrated in FIG. 2, the first valve 126 is maintained within the second volume 132 by the retaining feature 142.

The second connector 104 can include any number of similar features as compared to those described above with respect to the first connector 102. For example, in an embodiment, the second connector 104 includes a second valve 150 disposed in a valve area 152. The second valve 150 can translate between a first volume 154 and a second volume 156 of the valve area 152. The second connector 104 can also include a seal (not illustrated). In an embodiment, the first connector 102 can include a portion or feature 158 adapted to bias the second valve 150 from the first volume 154 into the second volume 156.

Figure 3:
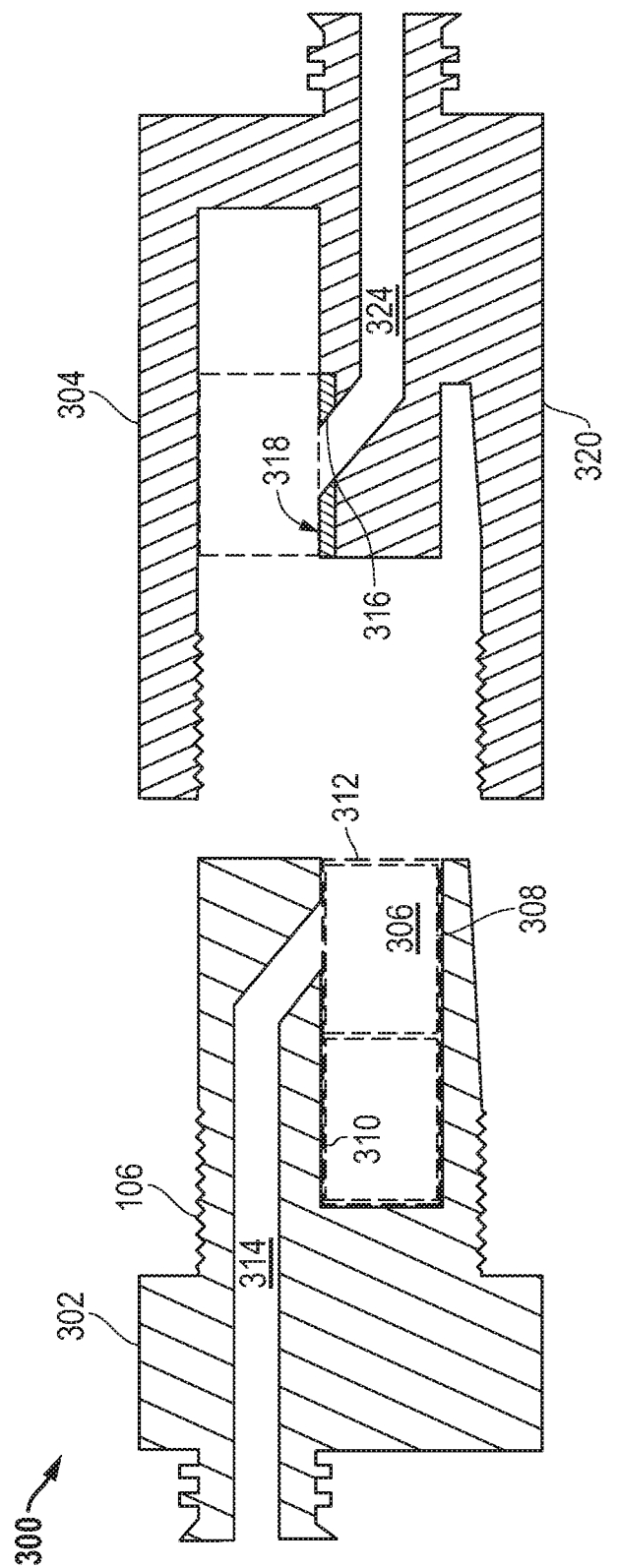
FIG. 3 includes a cross-sectional schematic view of a tubular coupling in accordance with another embodiment prior to coupling a first connector and a second connector.
Figure 4:
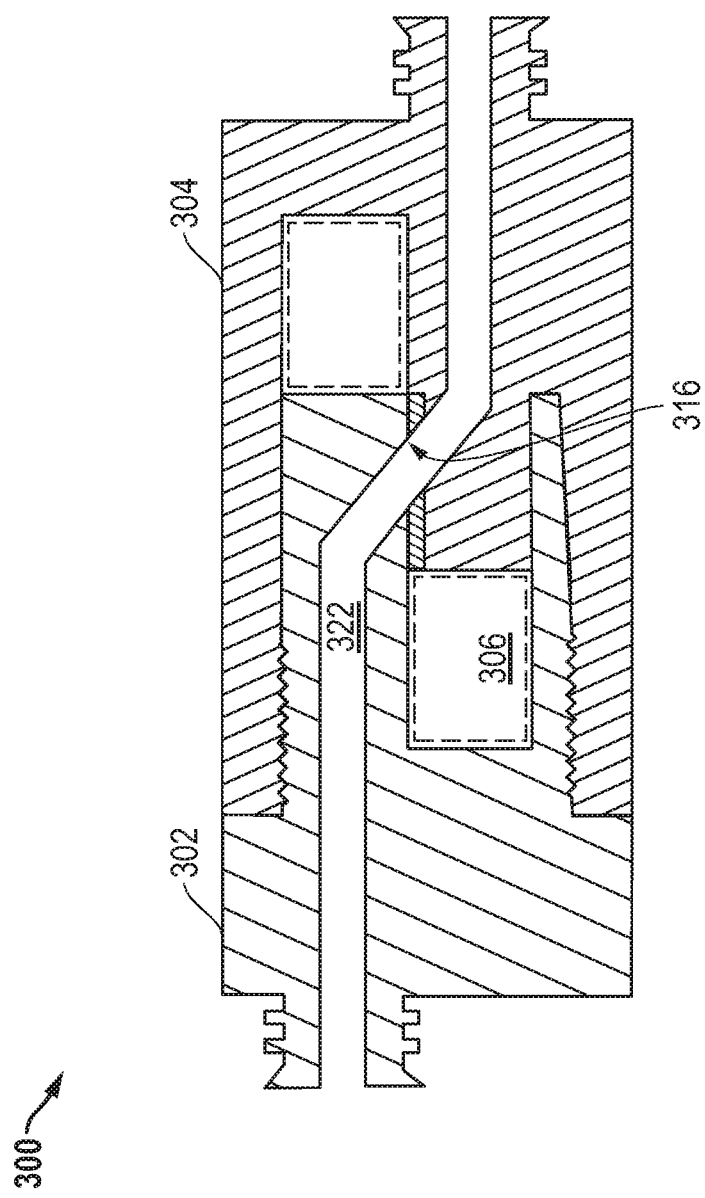
FIG. 4 includes a cross-sectional schematic view of the tubular coupling of FIG. 3 in accordance with an embodiment after coupling the first connector and the second connector.

FIGS. 3 and 4 include cross-sectional schematic views of a connector 300 including first and second connectors 302 and 304 in accordance with another embodiment. First connector 302 and second connector 304 can have any number of features or characteristics similar or different to the first and second connectors 102 and 104 described above. For example, the first connector 302 can include a first valve 306 translatable between first and second volumes 308 and 310 of a valve area 312 of the first connector 302. In the illustrated embodiment, the first and second volumes 308 and 310 of the valve area 312 share a similar dimension. More particularly, there is no visual feature defining the boundaries of the first and second volumes 308 and 310. In such embodiments, the first and second volumes 308 and 310 of the valve area 312 can be defined by locations in the valve area 312 where flow can occur and cannot occur through the first passageway portion 314.

In the embodiment illustrated in FIGS. 3 and 4, the second connector 304 can include a seal 316. The seal 316 can have a generally planar sealing surface 318. The seal 316 can be embedded, such as partially embedded, within the body 320 of the second connector 304. When mated, the surface 318 of the seal 316 can seal a continuous fluid passageway 322 formed by the first passageway portion 314 and a second passageway portion 324 of the second connector 304.

Figure 5:
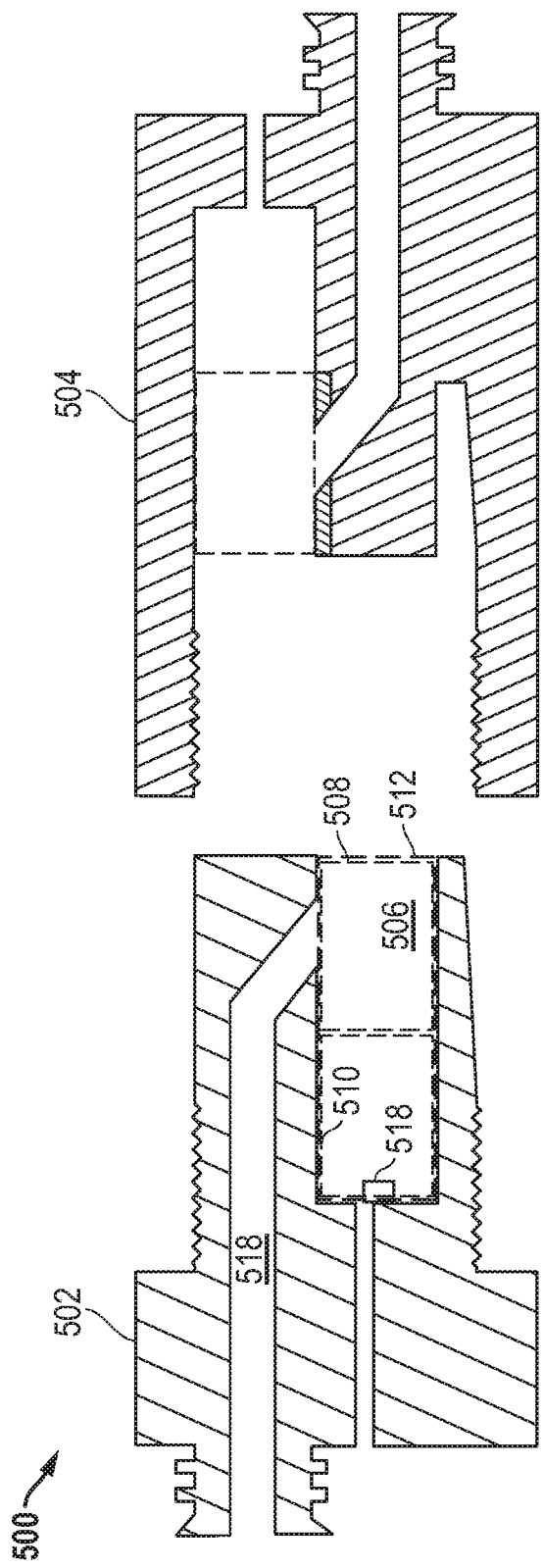
FIG. 5 includes a cross-sectional schematic view of a tubular coupling in accordance with another embodiment prior to coupling a first connector and a second connector.
Figure 6:
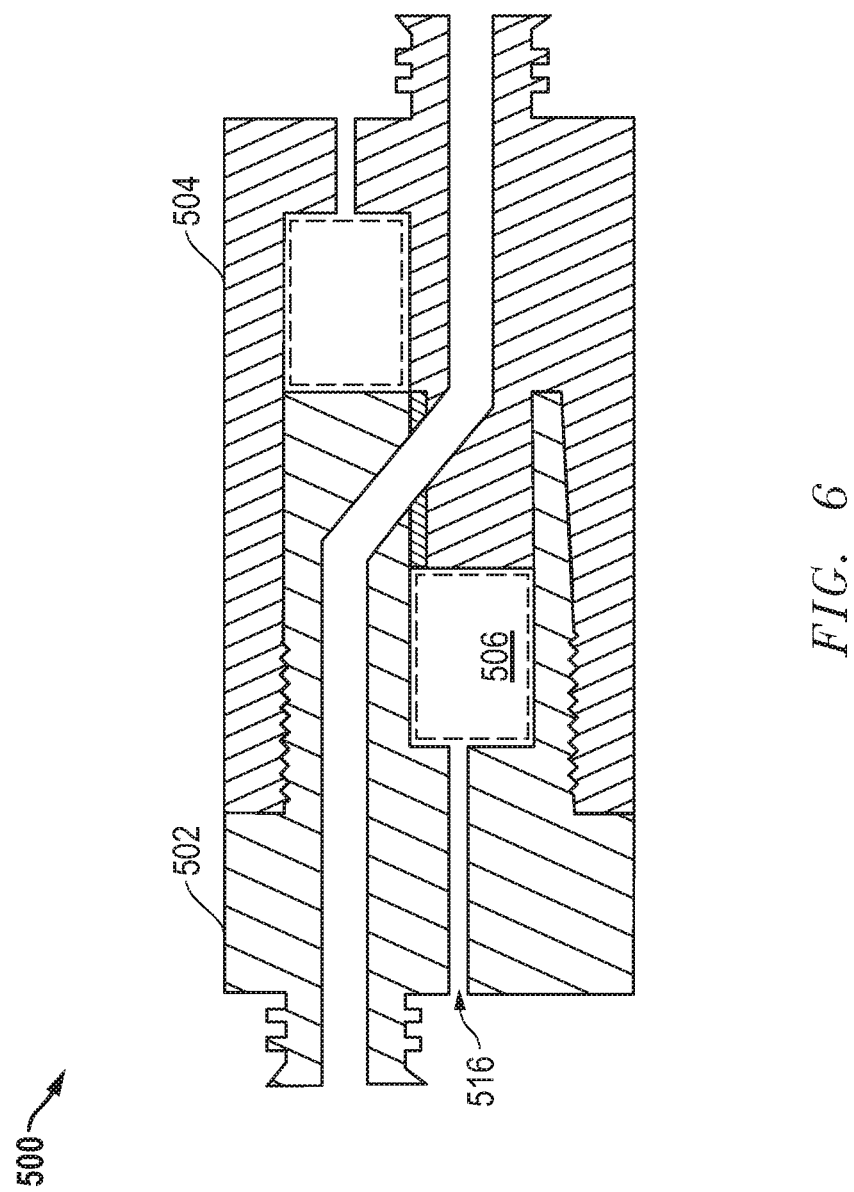
FIG. 6 includes a cross-sectional schematic view of the tubular coupling of FIG. 5 in accordance with an embodiment after coupling the first connector and the second connector.

FIGS. 5 and 6 include a cross-sectional schematic view of a connector 500 including first and second connectors 502 and 504 in accordance with another embodiment. First connector 502 and second connector 504 can have any number of features or characteristics similar or different to the first and second connectors 102/302 and 104/304 described above. For example, the first connector 502 can include a first valve 506 translatable between first and second volumes 508 and 510 of a valve area 512 of the first connector 502.

In an embodiment, the first connector 502 can include a channel 516 extending between the valve area 512 and an external environment 514. In a more particular embodiment, the channel 516 can extend between the second volume 510 and the external environment 514. In an embodiment, the channel 516 extends along a line generally parallel with the central axis of a first passageway portion 518 of the first connector 502. In another embodiment, the channel 516 has a cross-sectional area less than a cross-sectional area of the first passageway portion 518. In yet a further embodiment, the channel 516 has a cross-sectional area less than a cross-sectional area of the second volume 510 of the valve area 512.

In an embodiment, the channel 516 can include a channel seal (not illustrated) adapted to prevent fluid communication between the channel 516 and the external environment 514. In a particular embodiment, the channel seal is disposed at a location external to the second volume 510 of the valve area 512. In another embodiment, the channel seal is disposed at a location internal to the second volume 510. The channel 516 can be adapted to permit airflow between the second volume 510 of the valve area 512 and the external environment 514. In such a manner, the first valve 506 may more easily translate from the first volume 508 to the second volume 510 without raising pressure of the second volume 510. In a non-illustrated embodiment, the first valve 506 can include one or more features adapted to permit translation to the second volume 510 without raising pressure of the second volume 510 (e.g., holes, permeability, vents, secondary channels).

In an embodiment, the first valve 506 can be biased by a biasing element 518. In an embodiment, the biasing element can include a spring, hydraulics, air bladders, or any other biasing agent. In a particular embodiment, the biasing element 518 can include a coil spring. The biasing element 518 can be adapted to bias the first valve in a direction from the second volume 510 of the valve area 512 to the first volume 508 of the valve area 512. In the illustrated embodiment, the biasing element 518 is disposed at least in part in the second volume 510 of the valve area 512.

EMBODIMENTS

Embodiment 1

A tubular coupling comprising:
a first connector comprising:
  a body defining a first passageway portion and a valve area, the valve area comprising:
    a first volume adjacent to an end of the first passageway portion; and
    a second volume in fluid communication with the first volume; and
  a first valve disposed in the first volume of the valve area; and
a second connector adapted to receive at least a portion of the first connector, the second connector comprising:
  a body defining a second passageway portion and a valve area, the valve area comprising:
    a first volume adjacent to an end of the second passageway portion; and
    a second volume in fluid communication with the first volume; and
  a second valve disposed in the first volume of the valve area,
wherein the first and second valves are adapted to translate into the second volumes of the first and second connectors, and wherein the first and second passageway portions are adapted to be in fluid communication when the first and second valves are disposed in the second volumes of the first and second connectors.

Embodiment 2

A first connector comprising:
a body defining a first passageway portion and a valve area, the valve area comprising:
  a first volume adjacent to an end of the first passageway portion; and a second volume in fluid communication with the first volume; and a first valve disposed in the first volume of the valve area, wherein the first valve is adapted to translate into the second volume when the first connector is coupled with a second connector, and wherein the first and second passageway portions are adapted to be in fluid communication when the first and second valves are disposed in the second volumes of the first and second connectors.

Embodiment 3

A method of coupling tubulars comprising:
providing a first connector coupled to a first tubular and a second connector coupled to a second tubular, wherein the first connector comprises a body defining a first passageway portion and a valve area and the second connector comprises a body defining a second passageway portion and a valve area;
translating the first and second connectors together until a valve within first connector moves from a first volume of the valve area of the first connector to a second volume of the valve area and a valve within the second connector moves from a first volume of the valve area of the second connector to a second volume of the valve area; and
initiating a fluid flow through the tubulars.

Embodiment 4

The tubular coupling, first connector, or method of any one of the preceding embodiments, wherein the first valve is adapted to translate from the first volume of the first connector to the second volume of the first connector upon urging the first and second connectors together, wherein the first valve is urged from the first volume of the first connector to the second volume of the first connector by a portion of the second connector, wherein the second connector comprises a feature adapted to urge the first valve into the second volume of the valve area.

Embodiment 5

The tubular coupling, first connector, or method of any one of the preceding embodiments, wherein the first volume of the first connector has a tapered sidewall, wherein the first volume defines a ramped surface, wherein the first volume has a first cross-sectional width at a location adjacent to the second volume and a second cross-sectional width as a location opposite the second volume, and wherein the first cross-sectional width is less than the second cross-sectional width.

Embodiment 6

The tubular coupling, first connector, or method of any one of the preceding embodiments, wherein the first volume of the second connector has a tapered sidewall, wherein the first volume defines a ramped surface, wherein the first volume has a first cross-sectional width at a location adjacent to the second volume and a second cross-sectional width as a location opposite the second volume, and wherein the first cross-sectional width is less than the second cross-sectional width.

Embodiment 7

The tubular coupling, first connector, or method of any one of the preceding embodiments, wherein the first valve comprises a polymer, wherein the first valve comprises a low friction polymer, wherein the first valve comprises a fluoropolymer, wherein the first valve comprises a fluoropolymer coating, wherein the first valve comprises a low friction coating, wherein the first valve comprises an elastomeric material, wherein the first valve comprises a rubber, wherein the first valve comprises a synthetic rubber, wherein the first valve comprises an elastomeric core and an outer coating, wherein the first valve comprises a multipart construction.

Embodiment 8

The tubular coupling, first connector, or method of any one of the preceding embodiments, wherein the body of at least one of the first and second connectors comprises at least one of a plastic such as a thermoplastic, a thermoset, or a rubber, and a metal.

Embodiment 9

The tubular coupling, first connector, or method of any one of the preceding embodiments, wherein the first and second connectors are adapted to secure to one another via a bayonet connection, an interference fit, engageable fasteners, another suitable method, or any combination thereof.

Embodiment 10

The tubular coupling, first connector, or method of any one of the preceding embodiments, wherein the second volume of the first connector has a volume greater than a volume of the first valve.

Embodiment 11

The tubular coupling, first connector, or method of any one of the preceding embodiments, wherein the first connector has a retaining feature adapted to maintain the first valve in the second volume of the valve area after the first valve is urged into the second volume, wherein the retaining feature comprises an end surface of a tapered sidewall of the first volume.

Embodiment 12

The tubular coupling, first connector, or method of any one of the preceding embodiments, further comprising a seal disposed in the first connector, wherein the seal is disposed adjacent to the end of the first passageway portion, wherein the seal contacts the first valve when the first valve is disposed in the first volume of the valve area, wherein the seal is spaced apart from the first valve when the first valve is disposed in the second volume of the valve area, wherein the seal is adapted to contact the second connector when the first valve is disposed in the second volume of the valve area.

Embodiment 13

The tubular coupling, first connector, or method of embodiment 12, wherein the seal is disposed between the first valve and the body of the first connector when the first valve is disposed in the first volume of the valve area of the first connector, and wherein the seal is disposed between the body of the first connector and the body of the second connector when the first valve is disposed in the second volume of the valve area of the first connector.

Embodiment 14

The tubular coupling, first connector, or method of any one of the preceding embodiments, wherein the first passageway portion is disconnected from an external environment when the first valve is disposed in the first volume of the valve area of the first connector, wherein the second passageway portion is disconnected from the external environment when the second valve is disposed in a first volume of a valve area of the second connector, wherein the first and second passageway portions are in fluid communication when the first and second valves are disposed in the second volumes of the valve areas of the first and second connectors.

Embodiment 15

The tubular coupling, first connector, or method of any one of the preceding embodiments, wherein the first valve is spaced apart from the first passageway portion when the first valve is disposed in the second volume of the valve area of the first connector, and wherein the second valve is spaced apart from the second passageway portion when the second valve is disposed in the second volume of the valve area of the second connector.

Embodiment 16

The tubular coupling, first connector, or method of any one of the preceding embodiments, wherein the body of the first connector defines a channel extending from the second volume of the valve area to an external environment, wherein the channel extends generally parallel with the first passageway portion, wherein the channel has a cross-sectional area less than a cross-sectional area of the first passageway portion, wherein the channel comprises a channel seal adapted to prevent fluid communication between the channel and an external environment, wherein the channel is adapted to vent air from the valve area to an external environment as the first valve is translated into the second volume of the valve area.

Embodiment 17

The tubular coupling, first connector, or method of any one of the preceding embodiments, wherein the body of the first connector comprises:
  a base portion; and
  an engagement portion extending from the base portion, wherein the engagement portion is adapted to extend coaxial with an engagement portion of the second connector, and wherein the base portion is spaced apart from the second connector.

Embodiment 18

The tubular coupling, first connector, or method of embodiment 17, wherein the engagement portion of the first connector has a first ramped surface, wherein the engagement portion of the second connector has a second ramped surface, and wherein the first and second ramped surfaces are adapted to interact during coupling of the first and second connectors, and wherein translating the first and second connectors together deforms at least a portion of the first and second connectors to maintain the first and second valves in the second volumes of the valve areas.

Embodiment 19

The tubular coupling, first connector, or method of any one of the preceding embodiments, further comprising a cap removably coupled to an end of the first connector, wherein the cap is adapted to maintain the first passageway portion in a septic state.

Embodiment 20

The tubular coupling, first connector, or method of any one of the preceding embodiments, wherein the first connector further comprises a biasing element adapted to bias the first valve, wherein the biasing element comprises a spring, wherein the biasing element is adapted to bias the first valve in a direction from the second volume of the valve area to the first volume of the valve area, wherein the biasing element is disposed at least in part in the second volume, wherein the biasing element comprises a coil spring, wherein the biasing element comprises a piston, wherein the biasing element comprises an air bladder.

Embodiment 21

The tubular coupling, first connector, or method of any one of the preceding embodiments, wherein the first and second passageway portions are adapted to form a continuous passageway in the connected state, and wherein the continuous passageway has a generally S-shaped cross-sectional profile, wherein the continuous passageway has a straight cross-sectional profile.

Embodiment 22

The tubular coupling, first connector, or method of any one of the preceding embodiments, wherein the tubular coupling is reusable, wherein the tubular coupling is adapted for single-use.

Embodiment 23

The tubular coupling, first connector, or method of any one of the preceding embodiments, wherein the body of the first connector comprises an opening, and wherein the opening is disposed along the valve area, wherein the opening is in open communication with the first volume of the valve area, wherein the opening is adapted to provide a viewing area into the valve area, wherein the opening is adapted to provide a viewing area into the first volume of the valve area.

Embodiment 24

The tubular coupling, first connector, or method of any one of the preceding embodiments, wherein the first passageway portion comprises at least two passageway portions, wherein the at least two passageway portions are in fluid communication, wherein a first of the at least two passageway portions is adapted to couple with the second connector, and wherein the second of the at least two passageway portions is adapted to couple with a third connector.

Note that not all of the features described above are required, that a portion of a specific feature may not be required, and that one or more features may be provided in addition to those described. Still further, the order in which features are described is not necessarily the order in which the features are installed.

Certain features are, for clarity, described herein in the context of separate embodiments, may also be provided in combination in a single embodiment. Conversely, various features that are, for brevity, described in the context of a single embodiment, may also be provided separately or in any subcombinations.

Benefits, other advantages, and solutions to problems have been described above with regard to specific embodiments, However, the benefits, advantages, solutions to problems, and any feature(s) that may cause any benefit, advantage, or solution to occur or become more pronounced are not to be construed as a critical, required, or essential feature of any or all the claims.

What is claimed is:

1. A tubular coupling comprising:
a first connector comprising:
a body defining a first passageway portion and a valve area, the valve area offset from a main centerline of the first passageway portion, wherein the first passageway portion is a static conduit within the body and wherein the valve area comprises:
a first volume adjacent to an end of the first passageway portion; and
a second volume in fluid communication with the first volume; and
a first valve disposed in the first volume of the valve area;
and
a second connector adapted to receive at least a portion of the first connector, the second connector comprising:
a body defining a second passageway portion and a valve area, the valve area offset from a main centerline of the second passageway portion, wherein the second passageway portion is a static conduit within the body and wherein the valve area comprises:
a first volume adjacent to an end of the second passageway portion; and
a second volume in fluid communication with the first volume;
a seal at an end of the second passageway portion; and
a second valve disposed in the first volume of the valve area;
wherein the first and second valves are adapted to translate into the second volumes of the first and second connectors, wherein the second volumes of the first and second connectors are free of a spring, wherein the first and second valves are retained in the second volume after the first and second valves are translated into the second volume and wherein the first and second passageway portions are adapted to be in fluid communication when the first and second valves are disposed in the second volumes of the first and second connectors.

2. The tubular coupling of claim 1, wherein the first valve is adapted to translate from the first volume of the first connector to the second volume of the first connector upon urging the first and second connectors together.

3. The tubular coupling of claim 1, wherein the first volume of the first connector has a tapered sidewall.

4. The tubular coupling of claim 1, wherein the first volume of the second connector has a tapered sidewall.

5. The tubular coupling of claim 1, wherein the first valve comprises a polymer.

6. The tubular coupling of claim 1, wherein the body of at least one of the first and second connectors comprises at least one of a plastic such as a thermoplastic, a thermoset, or a rubber, and a metal.

7. The tubular coupling of claim 1, wherein the first and second connectors are adapted to secure to one another via a bayonet connection, an interference fit, engageable fasteners, or any combination thereof.

8. The tubular coupling of claim 1, wherein the second volume of the first connector has a volume greater than a volume of the first valve.

9. The tubular coupling of claim 1, wherein the first connector has a retaining feature adapted to maintain the first valve in the second volume of the valve area after the first valve is urged into the second volume.

10. The tubular coupling of claim 1, further comprising a seal disposed in the first connector.

11. The tubular coupling of claim 1, wherein the first passageway portion is disconnected from an external environment when the first valve is disposed in the first volume of the valve area of the first connector.

12. The tubular coupling of claim 1, wherein the second passageway portion is disconnected from the external environment when the second valve is disposed in the first volume of the valve area of the second connector.

13. The tubular coupling of claim 1, wherein the first valve is spaced apart from the first passageway portion when the first valve is disposed in the second volume of the valve area of the first connector, and wherein the second valve is spaced apart from the second passageway portion when the second valve is disposed in the second volume of the valve area of the second connector.

14. The tubular coupling of claim 1, wherein the body of the first connector defines a channel extending from the second volume of the valve area to an external environment.

15. The tubular coupling of claim 1, wherein the body of the first connector comprises:
a base portion; and
an engagement portion extending from the base portion, wherein the engagement portion is adapted to extend coaxial with an engagement portion of the second connector, and wherein the base portion is spaced apart from the second connector.

16. The tubular coupling of claim 1, wherein the first and second passageway portions are adapted to form a continuous passageway in the connected state.

17. A connector comprising:
a body defining a passageway portion and a valve area, the valve area offset from a main centerline of the passageway portion, wherein the passageway portion is a static conduit within the body and wherein the valve area comprises:
a first volume adjacent to an end of the passageway portion;
a second volume in fluid communication with the first volume;
a seal at an end of the passageway portion; and
a first valve disposed in the first volume of the valve area,
wherein the first valve is adapted to translate into the second volume when the connector is coupled with a complimentary connector, wherein the second volume is free of any bias, wherein the first valve is retained in the second volume after the first valve is translated into the second volume and wherein the connectors are adapted to be in fluid communication when the first valve is disposed in the second volume of the connector.

18. A method of coupling tubulars comprising:
providing a first connector coupled to a first tubular and a second connector coupled to a second tubular, wherein the first connector comprises a body defining a first passageway portion and a valve area, the valve area offset from a main centerline of the first passageway portion and the second connector comprises a body defining a second passageway portion and a valve area, the valve area offset from a main centerline of the second passageway portion, and a seal at an end of the second passageway portion, wherein the first passageway portion is a static conduit within the body of the first connector and the second passageway portion is a static conduit within the body of the second connector;
translating the first and second connectors together until a first valve within the first connector moves from a first volume of the valve area of the first connector to a second volume of the valve area and a second valve within the second connector moves from a first volume of the valve area of the second connector to a second volume of the valve area, wherein the second volumes of the first and second connectors are free of a spring, wherein the first and second valves are retained in the second volume after the first and second valves are translated into the second volume; and
initiating a fluid flow through the tubulars.

\* \* \* \* \*